United States Patent
Nam

(10) Patent No.: US 12,290,547 B2
(45) Date of Patent: May 6, 2025

(54) STAMINA-IMPROVING COMPOSITION AND STAMINA-IMPROVING NATURAL TEA COMPRISING SAME

(71) Applicant: Jong Hyun Nam, Seoul (KR)

(72) Inventor: Jong Hyun Nam, Seoul (KR)

(*) Notice: Subject to any disclaimer, the term of this patent is extended or adjusted under 35 U.S.C. 154(b) by 607 days.

(21) Appl. No.: 17/687,939

(22) Filed: Mar. 7, 2022

(65) Prior Publication Data
US 2022/0184168 A1 Jun. 16, 2022

Related U.S. Application Data

(63) Continuation of application No. PCT/KR2020/006538, filed on May 19, 2020.

(30) Foreign Application Priority Data

Apr. 3, 2020 (KR) .......................... 10-2020-0040817

(51) Int. Cl.
| | |
|---|---|
| *A61K 36/82* | (2006.01) |
| *A23F 3/00* | (2025.01) |
| *A61K 36/238* | (2006.01) |
| *A61K 36/355* | (2006.01) |
| *A61K 36/41* | (2006.01) |
| *A61K 36/48* | (2006.01) |
| *A61K 45/06* | (2006.01) |

(52) U.S. Cl.
CPC .............. *A61K 36/82* (2013.01); *A23F 3/00* (2013.01); *A61K 36/238* (2013.01); *A61K 36/355* (2013.01); *A61K 36/41* (2013.01); *A61K 36/48* (2013.01); *A61K 45/06* (2013.01)

(58) Field of Classification Search
CPC ... A23L 33/105; A61K 36/355; A61K 36/238; A61K 36/41; A61K 36/48
See application file for complete search history.

(56) References Cited

U.S. PATENT DOCUMENTS

| | | |
|---|---|---|
| 2003/0086983 A1 | 5/2003 | Nam |
| 2016/0213725 A1 | 7/2016 | Eom |
| 2019/0022161 A1 | 1/2019 | Kang |

FOREIGN PATENT DOCUMENTS

| | | | |
|---|---|---|---|
| CN | 101129711 A | | 2/2008 |
| CN | 104248545 A | * | 12/2014 |
| CN | 104547249 A | | 4/2015 |
| CN | 110227113 A | | 9/2019 |
| JP | 2002-265343 A | | 9/2002 |
| JP | 2011-519850 A | | 7/2011 |
| JP | 2016-537307 A | | 12/2016 |
| JP | 2018-57301 A | | 4/2018 |
| JP | 2019-507798 A | | 3/2019 |
| KR | 10-2016-0050764 A | | 5/2016 |
| KR | 10-2016-0059743 A | | 5/2016 |
| KR | 20190065084 A | * | 5/2016 |
| KR | 10-2017-0119468 A | | 10/2017 |
| KR | 10-2019-0065084 A | | 6/2019 |
| KR | 20160050764 A | * | 6/2019 |
| KR | 10-2019-0081545 A | | 7/2019 |
| KR | 10-2019-0106123 A | | 9/2019 |
| WO | 2009/133998 A1 | | 11/2009 |
| WO | 2015/046743 A1 | | 4/2015 |

OTHER PUBLICATIONS

Kreiner et al. Chinese J Nat Med, 2107, 15(4), 0255-0264.*
Leu et al. Int. J. Mol. Sci., 2012, 13, 9754-9768.*
Lee et al. Plant Disease, 2002, 86(4), 440.*
First Notification of Office Action and search report issued by the China National Intellectual Property Administration for Chinese Patent Application No. 202080062305.9, mailed on Jul. 1, 2023, with an English machine translation.
Second Notification of Office Action and search report issued by the China National Intellectual Property Administration for Chinese Patent Application No. 202080062305.9, mailed on Mar. 23, 2024, with an English machine translation.
He Daqing et al., "Anatomy and Physiology", Hubei Science and Technology Press, p. 287, 2007, with an English translation.
"Comprehensive Medical Guidance Book for the Qualification Examination for Practicing Assistant Physicians Integrating Traditional Chinese and Western Medicine", Traditional Chinese Medicine, Traditional Chinese Medicine Physician Qualification Certification Center of the National Drug Administration, p. 572, 2020, with an English translation.
He Wang, "Prostate: A Hidden Risk Organ for Men's Health", People's Military Medical Press, p. 12, 2005, with an English translation.
Jiayang Zhang et al., "Pharmaceutical Service Science", Southeast University Press, p. 108, 2017, with an English translation.
Notice of Reasons for Refusal issued by the Japan Patent Office for Japanese Patent Application No. 2022-516241, mailed on Apr. 18, 2023, with an English machine translation.
International Search Report issued by the Korean Intellectual Property Office for corresponding International Patent Application No. PCT/KR2020/006538, mailed on Jan. 15, 2022, with an English translation.
Notification Certificate of Substantive Examination issued by the Mexican Institute of Industrial Property for International Patent Application No. MX/a/2022/002932, dated Sep. 9, 2024, with an English machine translation.
Lee et al., "Orostachys japonicus A. Berger Extracts Induce Immunity-Enhancing Effects on Cyclophosphamide-Treated Immunosuppressed Rats", Hindawi, BioMed Research International, Jan. 2019, pp. 1-9, vol. 2019, Article ID 9461960.

* cited by examiner

*Primary Examiner* — Kyle A Purdy
(74) *Attorney, Agent, or Firm* — MYERS WOLIN, LLC

(57) ABSTRACT

A stamina-improving composition, a stamina-improving functional food including same and, more specifically, to a stamina-improving natural tea is provided. A stamina-improving composition including as an active ingredient at least one selected from *Orostachys japonicus* and *Vigna vexillata* var tsusimensis *Matsumura* is provided.

10 Claims, No Drawings

STAMINA-IMPROVING COMPOSITION AND STAMINA-IMPROVING NATURAL TEA COMPRISING SAME

CROSS-REFERENCE TO RELATED APPLICATION

This application is a continuation application of International Application PCT/KR2020/006538 filed on May 19, 2020 and designated the U.S., which claims priority to Korean Patent Application No. 10-2020-0040817, filed on Apr. 3, 2020. The contents of each are herein incorporated by reference.

TECHNICAL FIELD

The present invention relates to a stamina-improving composition, a stamina-improving functional food comprising same and, more specifically, to a stamina-improving natural tea.

BACKGROUND ART

Humankind having excellent intellectual abilities recognizes sex not only as a simple means of preserving the species, but also as an important means for leading a smooth and enjoyable family life. From ancient times, specifically men have constantly sought for strength or stamina improvement, and strong stamina was also considered a symbol of masculinity.

However, due to pollution from air, water resources, soil, etc. according to the advancement of industry, contamination and instantiation of food due to excessive use of pesticides and preservative treatment, severe stress in a fiercely competitive society, lack of exercise due to busy life, and so on, it has been reported through many literatures that the sexual ability of mankind, especially men, is seriously declining from various viewpoints, such as a decrease in sperm count.

Meanwhile, as material affluence increases, in particular, as the opportunity to be exposed to sexual stimulation enormously increases due to the development of mass media and the increase in netizens, interest in sex is further increasing.

Therefore, it can be said that today's men are in a disproportionate situation where their sexual abilities are generally lowered, while their interest in sex is increasing.

In this situation, the tendency of men to make up for the lowered sexual ability with stimulation by drugs is also increasing, but there would be a problem of side effects that the drug itself inevitably accompanies. For example, in recent years, sexual enhancement drugs developed in foreign countries are being widely marketed worldwide, but such drugs are reported to be fatal to patients with high blood pressure or heart disease and are disadvantageously expensive.

In addition, alcohol may be used in sex life by taking advantage of the fact that the alcohol relieves tension in the nervous system to some extent. However, when the amount of alcohol is very small, the alcohol can be helpful to some extent, but, when the intake thereof is increased, sexual performance may be significantly lowered. Moreover, if alcohol consumption becomes a habit, there is a risk of causing neurological and sexual dysfunction due to alcoholism.

Therefore, health supplement that is effective in improving men's strength or stamina without side effects has been desired for a long time.

DESCRIPTION OF EMBODIMENTS

Technical Problem

A first objective of the present invention is to provide a stamina-improving composition having a stamina improving effect.

A second objective of the present invention is to provide a stamina-improving composition having the effect of enhancing sperm vitality (motility).

A third objective of the present invention is to provide a functional food having a stamina effect.

Solution to Problem

In order to achieve the objective of the present invention, there is provided a stamina-improving composition comprising at least one selected from *Orostachys japonicus* and *Vigna vexillata* var *tsusimensis Matsumura* as an active ingredient.

According to an embodiment, the composition may further comprise *Albizia julibrissin*.

According to an embodiment, the composition may further comprise at least one selected from the group consisting of *Saposhnikoviae divaricata Schiskin* and *Lonicera caerulea* L var *edulis*.

According to an embodiment, at least one selected from *Orostachys japonicus* and protuberance may be included as a first raw material ingredient, and at least one selected from *Saposhnikoviae divaricata Schiskin* and *Lonicera caerulea* L var edulis may be included as a second raw material ingredient.

According to an embodiment, the first raw material ingredient and the second raw material ingredient are preferably in a weight ratio of the first raw material:the second raw material being 10 to 90 wt %:90 to 10 wt %.

According to an embodiment, the first raw material ingredient and the second raw material ingredient are preferably extracts extracted with one or more solvents selected from the group consisting of water, ethanol, and a mixture thereof.

In order to achieve another objective of the present invention, the present invention provides a stamina-improving health functional food, comprising the stamina-improving composition according to the present invention and a sitologically acceptable food supplement additive.

In order to achieve another objective of the present invention, the health functional food may have a formulation selected from the group consisting of powders, granules, tablets, capsules, candies, chewing gums, jellies and beverages.

According to an embodiment, the health functional food is preferably a health functional tea.

Advantageous Effects of Disclosure

As described above, the present invention is a novel useful invention pertaining to a beverage that is habitually consumed daily, such as tea, because it is easily drinkable while having no side effects, thereby obtaining an excellent stamina improving effect when consumed.

In addition, the stamina-improving composition according to the present invention can be added to various foods to enhance stamina without separately taking same in daily life.

In addition, the stamina-improving composition according to the present invention is composed of a natural material, and thus has no side effect, so that the composition can be concentrated to then be added to various drugs to help improve sexual function of people suffering from sexual dysfunction.

BEST MODE

Hereinafter, the present invention will be described in more detail. However, this is for specific description of the present invention and should not be construed as limiting the scope of the present invention.

The present invention provides a stamina-improving composition comprising *Orostachys japonicus* or *Vigna vexillata* var tsusimensis *Matsumura* as an active ingredient.

*Orostachys japonicus*, also called Orosrachys malacophyllus, is a plant of the family Crassulaceae and inhabits while being attached to sunny rock crevices in the mountains or the roof tiles and stone walls of traditional houses. However, *Orostachys japonicus* is hard to find these days and is on the verge of extinction, so that, for medicinal use, the *Orostachys japonicus* is artificially cultivated and propagated.

In the present invention, the term "*Vigna vexillata* var tsusimensis *Matsumura*", also called *Vigna angularis* var. nipponensis, grows on the seashore, and the roots are thick and straight. The stem of "*Vigna vexillata* var tsusimensis *Matsumura*" is about 3 m long, and there are brown spread hairs facing down on the petiole of the stem. The leaves of "*Vigna vexillata* var tsusimensis *Matsumura*" are alternate and consist of three small leaves. The small leaves have almost the same size and have hairs on both sides. The small leaf located at the end is narrow egg-shaped, 6-10 cm long, 3-4 cm wide, and has a sharp tip. The stipule is broad lanceolate and has distinct veins.

In the present invention, starch from seeds and roots of *Vigna vexillata* var tsusimensis *Matsumura* is used. Therefore, the seeds and roots can be extracted with water, an organic solvent, or a mixture thereof to be used.

According to an embodiment, the composition may further include *Albizia julibrissin*.

In the present invention, "*Albizia julibrissin*" includes both *Albizia julibrissin* DURAZZ and *Albizia coreana* NAKAI, and the leaves and/or barks of *Albizia julibrissin* can be used to obtain plant extracts.

According to the present invention, first, a dry sample of pulverized leaves or barks of naturally dried or hot-air dried *Albizia julibrissin* is mixed with water or an organic solvent in a weight ratio of 1:10 to 1:40, extracted at room temperature for more than 48 hours, and filtered. Thereafter, the filtrate is completely concentrated by using a vacuum reduced-pressure concentrator and dried in a freeze dryer, thereby obtaining a crude extract.

According to an embodiment, it is preferable to further comprise *Saposhnikoviae divaricata Schiskin* or *Lonicera caerulea* L var edulis in the composition.

*Saposhnikoviae divaricata Schiskin* is a triennial plant belonging to the family Umbelliferae of the order *Ostruthium* (masterwort), and is a perennial herb which is called Jinbangpung, Sanbanpung, Byungpunnamul, Sanbangpung tree, roots from Bangpung tree, etc, which grows in the dry sandy grassland. The long, round-shaped fruit of *Saposhnikoviae divaricata Schiskin* is blackish-brown, contains about 1,000 seeds, and weighs about 4 g.

The root, rhizome or fruit of *Saposhnikoviae divaricata Schiskin* may be used, but the root thereof is preferably used.

In the present invention, "*Lonicera caerulea* L var edulis" means to include all organs of natural, hybrid or varietal *Lonicera caerulea* L var edulis, such as roots, branches, stems, leaves, flowers and fruits, but preferably refers to fruits of *Lonicera caerulea* L var edulis. *Lonicera caerulea* L var edulis is a dicotyledonous plant that belongs to the family *Lonicera japonica* of the order *Rubia akane*, and is a 15 m tall deciduous shrub, in which the branches thereof are very branched, and shield-shaped bracts are present at nodes of small branches, and the inner part of the trunk thereof is white.

According to an embodiment, at least one selected from *Orostachys japonicus* and *Vigna vexillata* var tsusimensis *Matsumura* is preferably included as a first raw material ingredient and at least one selected from *Saposhnikoviae divaricata Schiskin* and *Lonicera caerulea* L var edulis is preferably included as a second raw material ingredient.

According to an embodiment, both of *Orostachys japonicus* and *Vigna vexillata* var tsusimensis *Matsumura* are preferably included as the first raw material ingredient, and when both are included, *Orostachys japonicus* and *Vigna vexillata* var tsusimensis *Matsumura* are preferably included in a weight ratio of 0.2-2:0.2-2.

Both of *Saposhnikoviae divaricata Schiskin* and *Lonicera caerulea* L var edulis are preferably included as the second raw material ingredient, and when both are included, *Saposhnikoviae divaricata Schiskin* and *Lonicera caerulea* L var edulis are preferably included in a weight ratio of 0.2-2:0.2-2.

According to an embodiment, the first raw material ingredient and the second raw material ingredient are preferably in a weight ratio of 10-90 wt %:90-10 wt %.

According to an embodiment of the present invention, the *Albizia julibrissin* extract added to the composition of the present invention is preferably included in an amount of 5 to 10 wt % of the composition.

The natural plant raw materials used in the present invention may be dried and used in the form of powders, but are preferably used after extracting same with water, an organic solvent, or a mixture thereof.

As the organic solvent used in the present invention, methanol, ethanol, acetone, ethyl acetate, ether, dichloromethane, hexane, or a mixture thereof may be used, and methanol or ethanol is preferably used. When water and an organic solvent are mixed and used, water and the organic solvent is preferably mixed in a weight ratio of 1-3:2-10.

In the plant extract according to the invention, these materials are mixed in a predetermined ratio (e.g., in a ratio of 1:1:1 to 2:1:1), for example, 5,000 ml of 80% ethanol is added to a total of 1 kg, and heated in a water bath at 95-100° C. for 12 hours to obtain the extract after installing a reflux cooler. The extract is cooled to about 50° C. and filtered through several layers of gauze to then obtain a supernatant.

Then, the extraction and filtration operations are repeated three times to combine the supernatant, which is then concentrated under reduced pressure by using a rotary evaporator. The concentrated supernatant is dissolved in a small amount of distilled water, and the finally obtained extract solution is freeze-dried at −80° C., thereby obtaining the plant extract according to the invention in the form of powder.

As a separate method, each plant material is cleaned, dried, cut into pieces, and put in a container. Then, the material and water are mixed in a ratio of 1:1 to 5 parts by weight, on the basis of weight, and then put in an autoclaved pot, followed by extracting at a temperature of 95 to 125° C.

for 2 to 5 hours, filtering and concentrating, thereby obtaining the plant extract according to the invention.

As a separate method, each plant material is washed thoroughly, cut into pieces, and then used as an extraction solution by extracting under a temperature of room temperature to 100° C., generally at room temperature (e.g., ±20) to about 45° C., and the extraction time is about 1 to 48 hours, which is, however, not restrictive but is arbitrary.

As used herein, the term "extract" is used to mean not only an extraction solution but also an extract which is powdered to a moisture content of 5 to 20% by using a drying means such as freeze drying, wind drying, heat drying, hot air drying, infrared drying, electromagnetic wave irradiation, etc. and a viscous extract having a water content of 20% or more.

According to an embodiment, the first raw material ingredient and the second raw material ingredient are preferably extracts extracted with one or more solvents selected from the group consisting of water, ethanol, and a mixture thereof.

In addition, vegetable oil may be included, and examples of usable vegetable oil may include soybean oil, sunflower oil, olive oil, grape seed oil, etc., which may be added in an amount of up to 0.01 to 5 wt % with respect to the total weight of the composition.

In order to achieve another objective of the present invention, the present invention provides a stamina-improving health functional food, comprising the stamina-improving composition according to the present invention and a sitologically acceptable food supplement additive.

In order to achieve another objective of the present invention, the health functional food preferably has a dosage form selected from the group consisting of powder, granules, tablets, capsules, candies, chewing gums, jellies and beverages.

According to an embodiment, the health functional food is preferably a health functional tea.

Health functional food is food that is prepared by adding same to food materials such as beverages, teas, etc. or by encapsulation, powdering, suspension, etc., and has a specific health effect when ingested, while having no side effects that may occur when taking a drug for a long period of time, because food is used as a raw material, unlike general drugs. The thus obtained health functional food of the present invention is very useful because it can be consumed on a daily basis. The amount of the stamina-improving composition added to such health food varies depending on the type of target health food and cannot be uniformly defined. However, the amount of the composition is generally in the range of 0.01 to 50 wt %, preferably 0.1 to 20 wt % with respect to the weight of the target food. In addition, in the case of food in the form of granules, tablets or capsules, the stamina-improving composition is generally added in an amount of 0.1 to 100 wt %, preferably 0.5 to 80 wt %.

According to another aspect of the present invention, a pharmaceutical stamina-improving composition may be provided by further adding a pharmaceutically acceptable carrier, excipient or diluent to the stamina-improving composition according to the present invention.

Advantages and features of the present invention, and methods of achieving same, will become apparent with reference to the embodiments described below in detail. However, the present invention is not limited to the embodiments disclosed below but will be embodied in various different forms, and only these embodiments allow the disclosure of the present invention to be complete and are provided so that this disclosure will be thorough and complete and will convey the aspects and features of the present disclosure to those skilled in the art. The present invention is merely defined by the scope of the appended claims.

Preparation Example 1

Preparation of Extracts

Preparation of *Orostachys japonicus* Extract 100 g of *Orostachys japonicus* was added to a mixed solvent of 300 g of purified water and 700 g of ethanol, followed by immersion extraction at room temperature for 72 hours. Thereafter, the extract was filtered with 300 mesh filter paper, filtered with No. 5C (1 μm, ADVANTEC), filtered with GF/C (1.2 μm, Glass microfiber filter, Whatman) filter paper, and then concentrated under reduced pressure and freeze-dried, thereby obtaining *Orostachys japonicus* extract powder.

Preparation of *Vigna vexillata* Var *tsusimensis Matsumura* Extract 100 g of *Vigna vexillata* var *tsusimensis Matsumura* roots and 100 g of seeds thereof were cut into pieces, and then *Vigna vexillata* var tsusimensis *Matsumura* root and seed extracts were prepared in the same manner as in the method for preparing the *Orostachys japonicus* extract.

Preparation of *Saposhnikoviae divaricata Schiskin* Extract

A *Saposhnikoviae divaricata Schiskin* extract was prepared in the same manner as in the method for preparing the *Orostachys japonicus* extract, except that 100 g of *Saposhnikoviae divaricata Schiskin* roots were used.

Preparation of *Lonicera caerulea* L Var Edulis Extract

A *Lonicera caerulea* L var edulis extract was prepared in the same manner as in the method for preparing the *Orostachys japonicus* extract, except that 100 g of each of *Lonicera caerulea* L var *edulis* roots, fruits and leaves were used.

Preparation of *Albizia julibrissin* Extract

An *Albizia julibrissin* extract was prepared in the same manner as in the method for preparing the *Orostachys japonicus* extract, except that 100 g of each of *Albizia julibrissin* leaves and barks were used.

EXAMPLES

Compositions were prepared by mixing each of the plant extract powders obtained in the preparation examples according to the ingredient compositions shown in Table 1 below.

TABLE 1

(wt %)

| Extract | Orostachys japonicus | Vigna vexillata var tsusimensis Matsumura Root | Vigna vexillata var tsusimensis Matsumura Seed | Saposhnikoviae divaricata Schiskin | Lonicera caerulea L var edulis Root | Lonicera caerulea L var edulis Fruit | Lonicera caerulea L var edulis Leaf | Albizia julibrissin Leaf | Albizia julibrissin Bark |
|---|---|---|---|---|---|---|---|---|---|
| Example 1 | 100 | | | | | | | | |
| Example 2 | | 100 | | | | | | | |
| Example 3 | | | 100 | | | | | | |
| Example 4 | 50 | | | 50 | | | | | |
| Example 5 | 50 | | | | 50 | | | | |
| Example 6 | 50 | | | | | 50 | | | |
| Example 7 | 50 | | | | | | 50 | | |
| Example 8 | 50 | 50 | | | | | | | |
| Example 9 | 25 | 25 | | 50 | | | | | |
| Example 10 | 25 | 25 | | 25 | 25 | | | | |
| Example 11 | 20 | 20 | | 20 | 20 | | | 20 | |
| Example 12 | 40 | | | 40 | | | | 20 | |
| Example 13 | | 50 | | | | 30 | | | 20 |

COMPARATIVE EXAMPLES

Compositions were prepared according to the ingredient compositions shown in Table 2 below.

TABLE 2

(wt %)

| Extract | Saposhnikoviae divaricata Schiskin | Lonicera caerulea L var edulis Root | Lonicera caerulea L var edulis Fruit | Lonicera caerulea L var edulis Leaf | Albizia julibrissin Leaf | Albizia julibrissin Bark |
|---|---|---|---|---|---|---|
| Comparative Example 1 | 100 | | | | | |
| Comparative Example 2 | | 100 | | | | |
| Comparative Example 3 | | | 100 | | | |
| Comparative Example 4 | | | | 100 | | |
| Comparative Example 5 | | | | | 100 | |
| Comparative Example 6 | | | | | | 100 |
| Comparative Example 7 | 50 | 50 | | | | |
| Comparative Example 8 | 50 | | | 50 | | |
| Comparative Example 9 | | 50 | | 50 | | |
| Comparative Example 10 | 25 | 25 | | | 50 | |

Experimental Example 1

To measure the stamina improving effect of the composition of the present invention, natural tea was prepared by mixing 1 g of the compositions prepared in Examples and Comparative Examples with 100 ml of water. For male test subjects in their 40s, 50s, 60s and 70s, each 140 cc of natural teas according to Examples and Comparative Examples were assigned to 10 people per age group (920 people in total), twice daily, that is, after breakfast and in the evening before going to bed, for 30 days, and satisfaction level for the respective natural teas were investigated. When offering natural teas, it was declared that 50% of the offered natural teas were genuine and effective while the remaining 50% were ineffective, thereby minimizing the contribution by the placebo effect, and blind testing was performed. The results are shown in Table 3 below.

Satisfaction levels were evaluated on a 5-point scale, and the average values (rounded) of 10 people for one natural tea were recorded.

TABLE 3

| | Aged in 40s | Aged in 50s | Aged in 60s | Aged in 70s |
|---|---|---|---|---|
| Example 1 | 4.0 | 3.5 | 3.4 | 1.5 |
| Example 2 | 4.1 | 3.6 | 3.5 | 1.0 |
| Example 3 | 4.2 | 3.4 | 2.8 | 1.2 |
| Example 4 | 4.5 | 3.0 | 3.0 | 1.8 |
| Example 5 | 4.6 | 3.7 | 3.5 | 1.9 |
| Example 6 | 4.3 | 3.0 | 3.4 | 1.6 |
| Example 7 | 4.4 | 3.4 | 3.0 | 1.4 |
| Example 8 | 4.2 | 3.0 | 3.1 | 1.0 |
| Example 9 | 4.5 | 3.6 | 3.5 | 1.0 |
| Example 10 | 4.6 | 3.5 | 3.0 | 1.2 |
| Example 11 | 4.9 | 4.0 | 3.1 | 1.0 |
| Example 12 | 4.8 | 4.1 | 3.8 | 1.5 |
| Example 13 | 4.7 | 4.2 | 3.5 | 1.6 |
| Comparative Example 1 | 2.5 | 2.4 | 1.8 | 0.5 |
| Comparative Example 2 | 2.4 | 2.0 | 1.5 | 0.6 |
| Comparative Example 3 | 2.2 | 2.1 | 1.6 | 0.1 |
| Comparative Example 4 | 2.1 | 2.0 | 2.0 | 0.9 |
| Comparative Example 5 | 2.4 | 2.0 | 1.5 | 1.0 |
| Comparative Example 6 | 2.5 | 2.1 | 1.4 | 0.6 |
| Comparative Example 7 | 3.0 | 2.1 | 2.0 | 0.9 |
| Comparative Example 8 | 2.4 | 2.0 | 1.2 | 0.2 |
| Comparative Example 9 | 2.5 | 2.2 | 1.0 | 0.1 |
| Comparative Example 10 | 2.0 | 1.8 | 1.5 | 0.4 |

The satisfaction level is a numerical value that each test subject feels personally and may vary depending on health and psychological conditions. However, as confirmed from Table 3, the composition according to the present invention, specifically the composition based on the first raw material, was effective evenly from the 40s to the 60s, whereas the compositions of Comparative Examples, in which the first raw material was not included, showed lowered effects as a whole.

Experimental Example 2

Animal Experiments on Inventive Natural Tea

When the stamina-improving natural teas of the present invention (natural teas of Examples 8, 9 and 12) were fed to experimental animals in the form of a beverage, changes in testis weight and sperm ability were measured.

The experimental method was performed under the following conditions.

Test period: 9 weeks

Experimental treatment: 4 treatment groups (control group treated with pure water and treatment groups treated with natural tea beverages of Examples 8, 9 and 12 of the present invention)

Experimental diet: Feeding Purina rat food

Experimental beverage: Fresh water or natural teas of Examples 8, 9 and 12 of the present invention were supplied everyday while keeping same in the refrigerator.

Experimental animals: 40 3-week-old S D rats were purchased and each 10 rats were allocated to each treatment group.

Measurement items: Growth rate, liver and testis weights, and sperm vitality and concentration The growth rate was recorded as the daily weight gain, and the testis weight was added up on both sides.

The experimental results will be described below.

The growth rate showed no statistically significant difference, but treatment groups of Examples 8, 9 12 had somewhat higher growth rates. With regard to testis weight, there was no difference between treatment groups. Meanwhile, the sperm vitality index classified into 5 scales was statistically higher in the treatment groups of Example 8, 9 and 12 than in the control group (P<0.05). With regard to the number of individuals having a vitality index of 5' or higher, no animals were present in the control group, whereas 6, 8, and 8 animals were found in the treatment groups of Example 8, 9 and 12, respectively. Meanwhile, no lesions were observed in the histopathological conditions for liver and testis tissues. These experimental results are shown in Table 4 below.

TABLE 4

| Measurement item (n = 10) | Treatment group | | | |
| --- | --- | --- | --- | --- |
|  | Control group | Example 8 | Example 9 | Example 12 |
| Starting weight (g) | 105 ± 15.1 | 106 ± 18.2 | 101 ± 14.3 | 102 ± 10.5 |
| End weight (g) | 345 ± 16.3 | 338 ± 28.5 | 340 ± 16.1 | 350 ± 20.1 |
| Testis weight (g) | 0.968 ± 0.055 | 0.978 ± 0.128 | 0.965 ± 0.105 | 0.957 ± 0.125 |
| Sperm vitality | 4.2 ± 0.5 | 4.9 ± 0.8 | 5.1 ± 0.4 | 5.0 ± 0.0 |
| Vitality index of 5' or higher | 0 | 6 | 8 | 8 |
| Sperm concentration ($\times 10^8$) | 15.05 ± 1.80 | 15.32 ± 1.90 | 16.05 ± 1.81 | 15.05 ± 1.88 |

From the results of Table 4, it is confirmed that the sperm vitality index and sperm concentration are significantly higher than those of the control group.

What is claimed is:

1. A composition for the improvement of sperm vitality or sperm concentration, comprising a) a mixture of the extract of the whole herb of *Orostachys japonicus* and the extract of the roots of *Vigna vexillata* var *tsusimensis Matsumura* which is included as a first raw material ingredient, and b) at least one extract selected from the extract of the roots of *Saposhnikoviae divaricata Schiskin* and the extract of the roots, fruits, or leaves of *Lonicera caerulea* L var *edulis* which is included as a second raw material ingredient, wherein the first raw material ingredient and the second raw material ingredient are in a weight ratio of first raw material:second raw material of 10 to 90 wt %: 90 to 10 wt %.

2. The composition of claim 1, further comprising *Albizia julibrissin*.

3. The composition of claim 1, wherein the first raw material ingredient and the second raw material ingredient are extracted with one or more solvents selected from the group consisting of water, ethanol, and a mixture thereof.

4. A composition according to claim 1 and a foodologically acceptable food supplement additive.

5. The composition of claim 4, further comprising a formulation selected from the group consisting of powders, granules, tablets, capsules, candies, chewing gums, jellies, and beverages.

6. The composition of claim 4, wherein the beverage is a health functional tea.

7. A composition according to claim 1 further comprising a pharmaceutically acceptable carrier, an excipient, or a diluent.

8. The pharmaceutical composition of claim 7, wherein the pharmaceutical composition has a formulation selected from the group consisting of tablets, pills, powders, granules, capsules, suspension emulsions, syrups, aerosols, external preparations, suppositories, and injections.

9. A method for improving stamina in a person in need thereof, which comprises administering to said person a therapeutically effective amount of a composition of claim 1.

10. A method of claim 9 wherein the stamina is sexual stamina.

\* \* \* \* \*